(12) United States Patent
Kleyman

(10) Patent No.: US 12,740,827 B2
(45) Date of Patent: Sep. 22, 2026

(54) METHOD AND END EFFECTOR FOR TISSUE ABLATION

(71) Applicant: Gennady I Kleyman, Brooklyn, NY (US)

(72) Inventor: Gennady I Kleyman, Brooklyn, NY (US)

(73) Assignee: Expandoheat, LLC, Hoboken, NJ (US)

( * ) Notice: Subject to any disclaimer, the term of this patent is extended or adjusted under 35 U.S.C. 154(b) by 733 days.

(21) Appl. No.: 17/169,941

(22) Filed: Feb. 8, 2021

(65) Prior Publication Data

US 2022/0249161 A1 Aug. 11, 2022

(51) Int. Cl.
*A61B 18/18* (2006.01)
*A61B 18/00* (2006.01)

(52) U.S. Cl.
CPC ..................... *A61B 18/1815* (2013.01); *A61B 2018/00059* (2013.01); *A61B 2018/0022* (2013.01); *A61B 2018/00577* (2013.01); *A61B 2018/00791* (2013.01); *A61B 2018/1861* (2013.01)

(58) Field of Classification Search
None
See application file for complete search history.

(56) References Cited

U.S. PATENT DOCUMENTS 5,057,106 A 10/1991 Kasevich et al.
5,843,144 A 12/1998 Rudie et al.
5,902,251 A 5/1999 vanHooydonk
6,002,968 A * 12/1999 Edwards ............ A61B 18/1477 606/41
6,041,260 A 3/2000 Stern et al.
6,366,818 B1 4/2002 Bolmsjo
6,427,089 B1 * 7/2002 Knowlton .............. A61B 18/18 607/101
6,447,505 B2 9/2002 McGovern et al.
8,521,302 B2 8/2013 Kleyman et al.
10,004,552 B1 * 6/2018 Kleyman ........... A61B 18/1815
2001/0008966 A1 * 7/2001 Arndt ....................... A61N 1/06 607/101
2005/0165389 A1 * 7/2005 Swain ................ A61B 18/1815 606/27

* cited by examiner

*Primary Examiner* — Sean W Collins
*Assistant Examiner* — Nora W Rhodes

(57) ABSTRACT

An end effector structure provided for an ablation apparatus, optionally having a covering balloon structure made from a compliant material such as rubber like materials, as for example silicone, including an antenna to emit microwave energy for cavity ablation that is covered with microwave energy absorbing and heat radiating material so that when end effector inserted into the body cavity, the balloon is filled up with liquid and balloon stretches to conform to a profile of the cavity to be ablated, and the applied microwave energy heats the liquid inside the balloon and heat energy to ablate or otherwise treat the body cavity tissue contacted with the compliant end effector. Other embodiments without the covering balloon apply heat directly to the cavity with the heated liquid.

15 Claims, 4 Drawing Sheets

METHOD AND END EFFECTOR FOR TISSUE ABLATION

FIELD OF THE INVENTION

The invention relates to cavity heating apparatus, in particular to tissue-treating devices for tissue ablation with heated fluid, such as ablation of a uterine cavity or an artery.

BACKGROUND OF THE INVENTION

Conventional medical devices used for thermal ablation operate by applying heat, either directly (e.g. by radiating microwave energy into the target site tissue), or indirectly to another structure that heats and ablates the target site tissue, for treatment of a target site biological tissue. Some prior devices also include an inflatable balloon that surrounds the source of heat energy, and is inserted into a cavity within a patient's body and utilizes a liquid to inflate the balloon after insertion. The liquid that expands the balloon remains in the balloon and is heated to operative temperature, maintained for a sufficient period of time to ablate of the selected tissue. Ablation devices that rely on conventional balloons and other inflatable treatment devices that apply heat from an internal wire resistance heater, require a long time to heat surrounding tissue by heat exchanged from the resistance heater through heated liquid and then through the balloon wall (when used) to the target tissue, and are unable to reliably heat the target tissue fast or reliably to the desired procedure temperature.

Prior devices may also have an active antenna located within the balloon to deliver microwave energy the balloon wall or membrane constructed of a compliant material loaded with lossy particles, i.e. particles that dissipate electromagnetic energy, or coated with a flexible material with lossy particles to allow the balloon to directly absorb microwave energy and generate heat. A disadvantage of such balloon structure and other conventional devices is that the lossy materials, e.g. ferrite or graphite particles, are substantially rigid and adding particles of such lossy material to the balloon wall or to the coating of the balloon wall (made as a thin layer of particles of such lossy material) results in the balloon wall becoming substantially rigid and lacking necessary stretch ability and ability to comply with cavity profile witch lead to big chance to fail to ablate all cavity wall. Also, since the balloon wall or the coating of the balloon wall are very thin it is impossible to completely absorb microwave energy and that causes substantial leakage of microwave energy, which results in uneven (excessive or insufficient) and unpredictable tissue heating.

SUMMARY

An exemplary embodiment of the present invention provides an end effector structure for tissue ablation powered by microwave energy source and end effector including a microwave antenna surrounded by a sleeve from microwave absorbing materials. Microwave absorbing material can include, by its nature and composition, material that absorbs microwave energy and emits heat in response to the absorbed microwave energy. Microwave absorbing material can also be a material that is itself transparent to microwave energy but impregnated with microwave absorbing particles, and has differing selectable microwave transmission and/or absorption characteristics at different locations along the microwave antenna to apply to the desired bi-tissue, a selective amount of microwave and/or heat energy. Exemplary microwave transparent material can be ceramic, silicone, fluorosilicone, fluorocarbon, thermoplastic rubber, ethyline propylene diene monomer, urethane etc. Exemplary microwave absorbing particles can be from nickel (Ni), copper (Cu), Aluminum (Al), Ag/Cu; Ag/Al; Ag/Ni; Ag/Glass, nickel-plated graphite, silver-plated aluminum, silver-plated copper, silver-plated nickel, silver-plated glass and pure silver etc.

"Volume resistivity" is a fundamental property that quantifies how strongly a given material opposes the flow of electric current. A low volume resistivity indicates a material that readily allows the flow of electric current. The international system unit of volume resistivity is the ohm-meter (Ω-m) or ohm-centimeter (ohm-cm). In case of microwave absorbing materials, when volume resistivity is high it means there are fewer microwave absorbing particles (fillers) in the microwave absorbing material and, correspondingly, less microwave energy will transfer into the heat energy and more microwave energy will be transmitted outside of microwave absorbing material. If the volume resistivity is lower, it means there are more microwave absorbing particles (fillers) in the microwave absorbing material and less microwave energy will be transmitted outside of microwave absorbing sleeve, and relatively less microwave energy will be transferred into the heat energy by the liquid.

When the microwave antenna, surrounded by and directly in contact with a sleeve having a length and comprising microwave absorbing material, emits microwave energy, the sleeve made from microwave absorbing material can comprise a high density of microwave absorbing particles will transfer higher percentage of antenna-radiated microwave energy into the heat energy and lower percentage of microwave energy will be transmitted thru the microwave absorbing sleeve. In this example, the liquid that is in contact with the sleeve will be heated by conduction from hot surface of the sleeve while the rest of the liquid will receive transmitted microwave energy that will generally be less than the energy received and absorbed by the sleeve. This heated liquid will ablate the tissue in direct contact or thru the balloon skin. The selected sleeve material for microwave absorption will affect the rate of temperature increase, so that the sleeve material (i.e. volume resistivity characteristic) can be chosen according to the particular ablation (or other) procedure performed.

In one embodiment, an end effector structure provided as an ablation apparatus, optionally includes a balloon structure made from a compliant material such as rubber-like materials, as for example silicone. An antenna to emit microwave energy for cavity ablation, is located inside the balloon and cover with microwave energy absorbing material and when end effector inserted into the body cavity, the balloon will filled up with liquid and balloon stretches to conform to a profile of the cavity to be ablated, and microwave energy will heat the liquid inside the balloon and heat energy will ablate the body cavity tissue contacted with the compliant end effector. Additionally as transmitted thru the liquid, the microwave energy will heat the cavity tissue and expedite the tissue heating process.

In another embodiment, an end effector structure is provided for an ablation apparatus, having an antenna to emit microwave to an antenna cover having a microwave energy absorbing material within the cover material. When end effector inserted into the body cavity, which is further filled up with liquid, microwave energy is radiated into the cover that will heat the liquid inside the cavity and heat energy is generated that will ablate the body cavity tissue. Alternate embodiments additionally radiate microwave energy through the antenna cover and transmitted into and/or through the surrounding liquid, providing microwave energy that will heat the balloon or directly to the cavity tissue and expedite or more closely control the heating process according to the selected procedure.

BRIEF DESCRIPTION OF THE DRAWING

The above and other aspects, features and advantages of the present invention will become more apparent from the following Detailed Description when taken in conjunction with the accompanying drawing in which.

DETAILED DESCRIPTION

Figures 1, 2, 3:
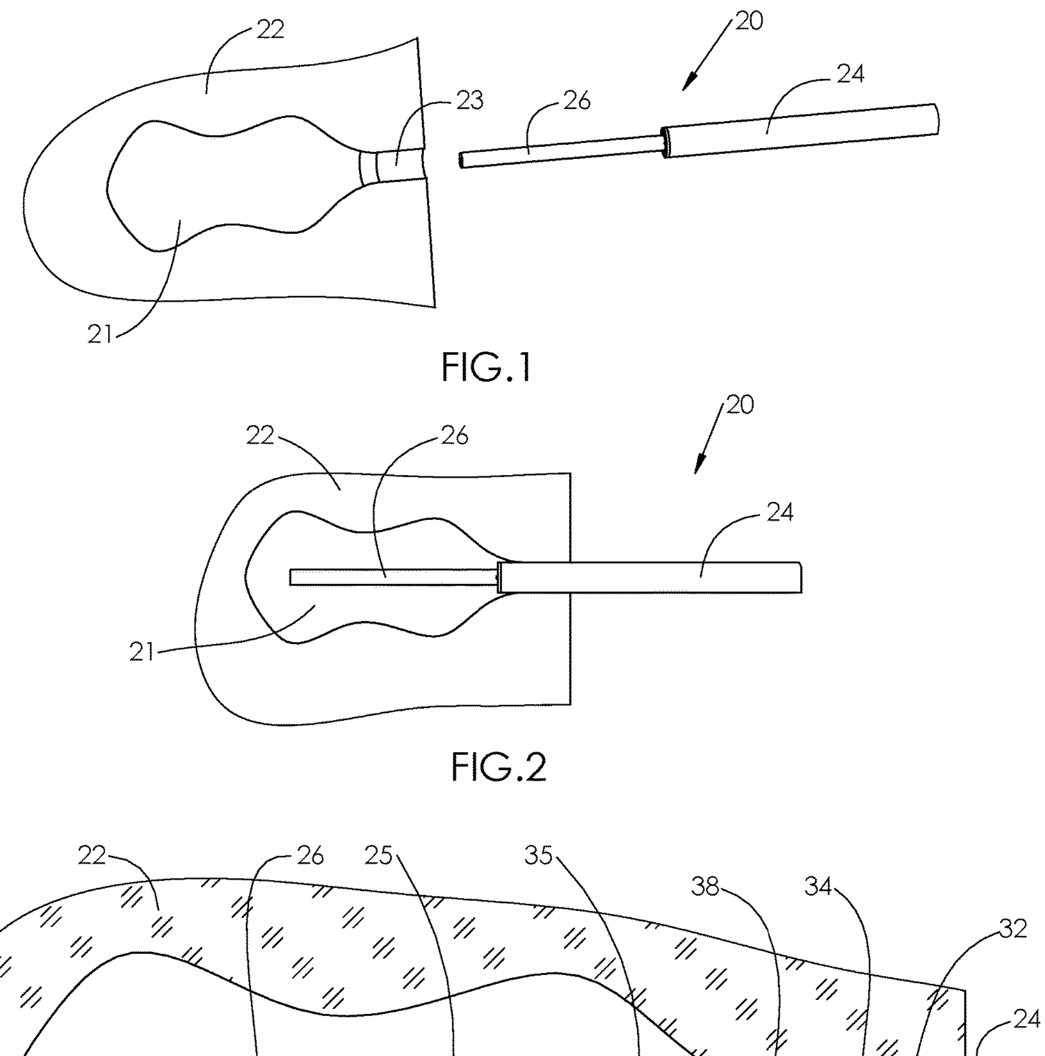
FIG. 1 is an isometric view one embodiment of the end effector according to the present invention before being inserted into a tissue cavity.
FIG. 2 is an isometric view of the end effector of FIG. 1 inserted into a cavity.
FIG. 3 is a sectional view of the end effector of FIG. 1.

Various embodiments of the present invention are described in detail with reference to the accompanying drawings. Wherever possible, the same or similar reference numerals are used in the drawings and the description to refer to the same or like parts or steps. In the following description, specific details are provided to provide an overall understanding of embodiments of the present invention and those skilled in the art will recognize that various changes and modifications of the embodiments described herein can be made without departing from the scope and spirit of the invention. Descriptions of well-known functions and constructions are omitted for the sake of clarity and conciseness. The term "microwave frequency range" refers herein to frequencies between 30 MHz and 30,000 MHz inclusive, where MHz is one million Hertz. Although the following description operates via a microwave energy emitter, the present invention is operable by various electromagnetic energy sources and is not limited to microwave energy.

FIG. 1 and FIG. 2 are views of first embodiment of present invention where tissue cavity ablation end effector 20 shown before and after been inserted into the tissue 22 cavity 21 opening 23. The end effector includes outside tubing 24 should preferably form a seal with the cavity opening 23 sufficient to retain fluid provided according to the present invention within the cavity 21. Furthermore, the embodiments according to the present invention include a sleeve 26 that become heated, and operable without direct contact with the tissue 2.

Figures 4, 5, 6, 7:
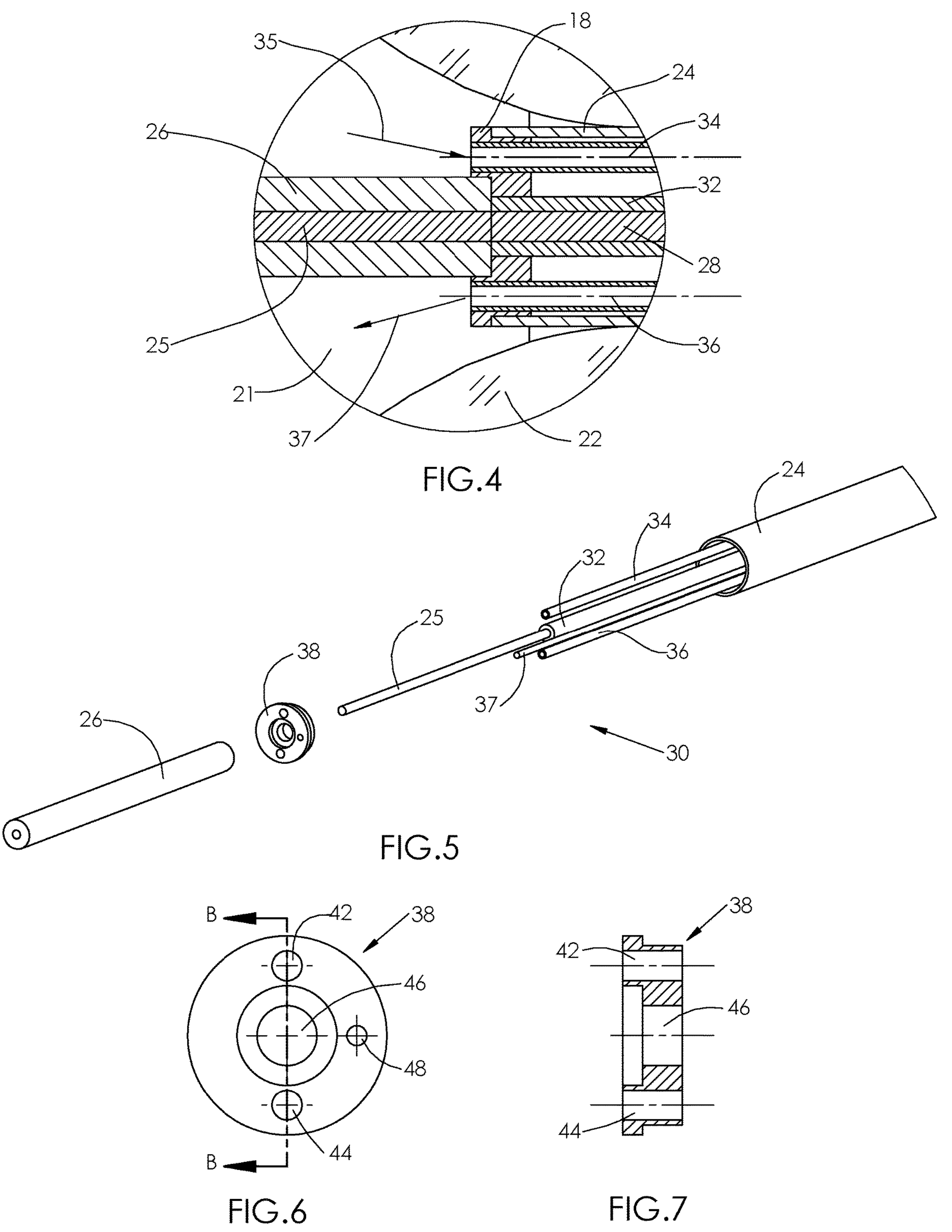
FIG. 4 is an enlarged view A taken from FIG. 3.
FIG. 5 is an exploded view of the end effector of the embodiment of FIG. 1.
FIG. 6 is a front view of end effector cap of the embodiment of FIG. 1.
FIG. 7 is a section B-B taken from FIG. 6.

As it shown on FIG. 3 and in further detail in FIG. 4, when end effector 20 is inserted into the cavity 21, liquid flow 37 is delivered into the cavity 21 to fill up the cavity thru the end effector fill tubing 36 (within outer tubing 24) and retained by a close fit of outside tubing 24 and tissue opening 23, connected to a source of liquid and means to deliver it (e.g. a pump) through the tubing 36. The liquid can be distillate water, dextrose in water or saline (or other suitable fluid). The end effector 20 includes a microwave antenna 25 covered by the sleeve 26 that is made from microwave absorbing materials. Microwave absorbing materials can be elastomer impregnated with dispersed particles that can be made from nickel, silver, copper, silver-coated copper, silver-coated aluminum, silver-coated glass, nickel-coated graphite filled silicone, silver-coated aluminum or nickel-coated graphite or other conductive materials capable of absorbing microwave energy and express the absorbed energy as heat that is received into the liquid surrounding the sleeve 26 within the cavity 21. The examples of the sleeve 26 conductive particles filled elastomers may include particle filled elastomers manufactured by Ja-Bar® such as material 802 where elastomer is silicone and filler is Ni/Cr.

The embodiments according to the present invention provide an end effector 20, shown in exploded view 30 in FIG. 5, include a microwave antenna 25 connected to the coaxial cable 32 conductor wire 28 that supplies microwave energy to the antenna 25. The coaxial cable 32 is connected to the source of microwave energy microwave generator (not shown) having sufficient power to heat the fluid filled cavity 21 interior according to the present invention. The end effector typically further includes a temperature measuring sensor 27 to monitor liquid temperature, a separate tubing 34 to evacuate liquid from the cavity 21 at the end of the procedure, when ablation of cavity 21 tissue 22 is finished. The temperature measuring sensor 27 can be a thermocouple, thermistor or fiber optic. The end effector tubing 24 includes an end cap 38, shown in FIGS. 6 and 7 that includes openings 46 sized to receive the antenna 25 and coaxial cable 32 therethrough with a close fit (or includes a seal) to restrict fluid outflow from the cavity, and openings 44 and 42 to receive the supply and removing liquid supply and removal tubings 16, 14 similarly fit to resist fluid outflow around tubings 16, 14, and opening 48 through which to receive the temperature sensor/probe 27 similarly fit, and to restrict fluid from flowing inside of the effector end 20.

After end effector 20 is inserted into the tissue 22 cavity 21 and be sufficiently sealed in the tissue opening 23, the cavity will be filled with liquid as supplied thru the supply tubing 36. When the tissue cavity 21 is full of liquid, microwave energy is applied to microwave antenna 25 to begin heating the sleeve 26 (and liquid in cavity with microwave energy not converted to heat by the sleeve 26). As one example, the sleeve 26 (with low volume resistivity) can be made from Ja-Bar® Silicone Corporation material 807, which is made of silicone with silver particles dispersed inside it. This material has volume resistivity 0.010 ohm-cm. End effector with this material will transfer more microwave energy into the heat and less microwave energy will be transmitted through it to the surrounding liquid.

As another example, the sleeve 26 (with high volume resistivity) made from material 852 from Ja-Bar® Silicone Corporation, which is made of silicone with nickel particles dispersed inside it, and it has volume resistivity of 2 ohm-cm. An end effector with this material will transfer less microwave energy into the heat and more microwave energy will be transmitted into the surrounding liquid.

When liquid temperature reaches a temperature selected according to the required parameters of the procedure, a signal from the temperature sensor 27, connected to a device, e.g. a switch, to stop or slow the supply of microwave energy to the antenna 25 from a microwave energy source.

When time of procedure is complete, the liquid will be removed from the cavity by way of exhaust tubing 34 (typically by suction) and end effector 20 will be removed from the tissue 22 cavity 21.

Figure 8:
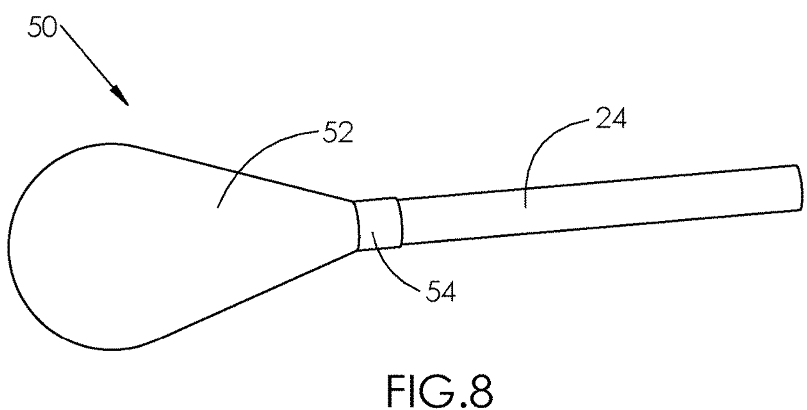
FIG. 8 is an isometric view of the end effector according to a second embodiment.
Figure 9:
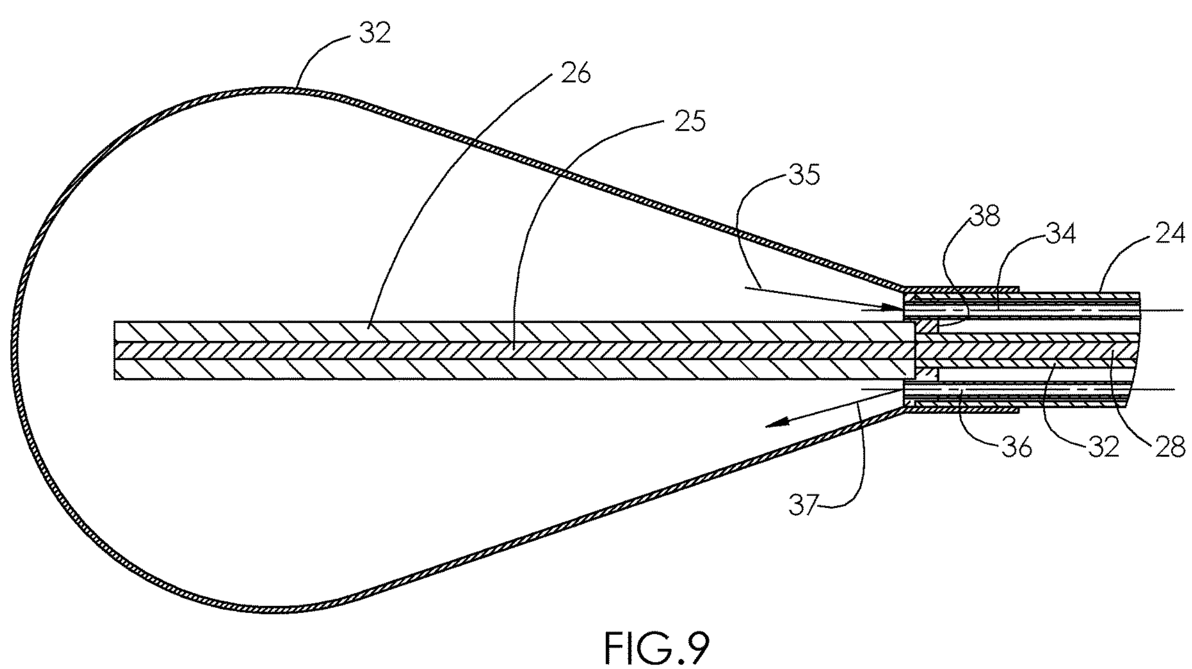
FIG. 9 is a sectional view of the end effector according to the embodiment of FIG. 8.

A second embodiment 50 of the present invention is shown in FIG. 8 and FIG. 9, where tissue cavity ablation end effector 50 substantially includes the embodiment 20, and additionally includes a balloon 52 (disposed over the end effector elements of embodiment 20) made from compliant material such as a silicone or similar rubber like material and sealed 54 over the tubing 24 end to contain the fluid within the balloon 52. When end effector 50 is inserted into the cavity 21, the liquid will be supplied and evacuated in same manner as in the prior embodiment, and further with the thin compliant balloon 52 that will adapt to cavity 21 profile and provide ablation of the cavity will be similar to first concept without direct tissue 22 contact with the liquid within the balloon 52. The liquid can be distillate water, dextrose in water or saline or liquid with microwave absorbing particles.

Figure 10:
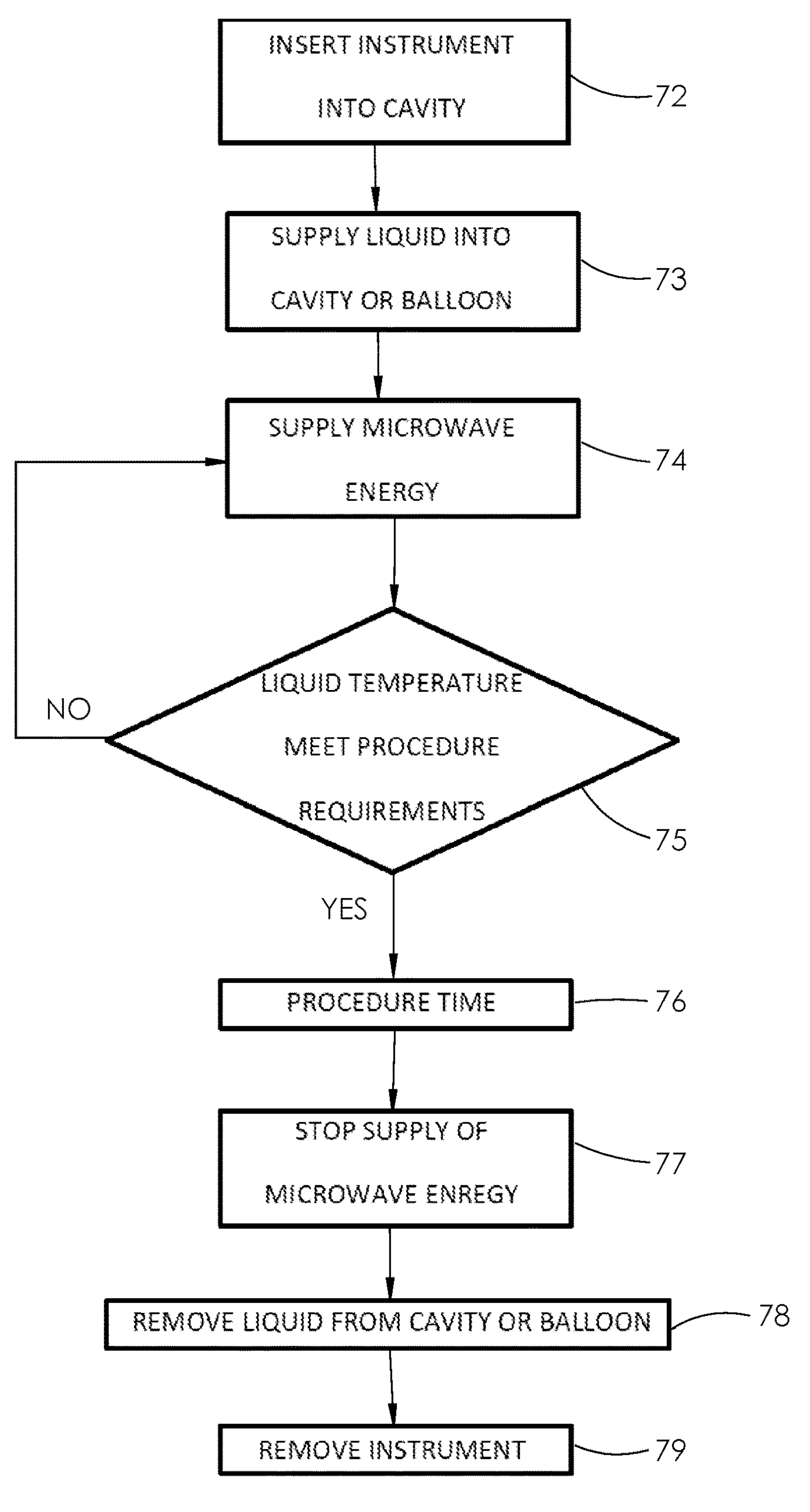
FIG. 10 is a flow chart diagram of an application of the embodiments according to the present invention.

A general logical flow chart 70 of ablation procedure according this invention FIG. 10, wherein 72 the end effector 20 (or 50) is inserted into a tissue 22 cavity 21 and sufficiently sealed at tissue 22 opening 23, whereupon 73 liquid is introduced into the cavity 21 and microwave energy is applied 74 to the antenna 25 via cable 32 and maintained 75 until the procedure requirements (e.g. tissue 22 temperature, etc.) are met. If the procedure requirements are met 75, and procedure time 76 has elapsed, then the microwave energy is turned off 77 and liquid is drained 78 from the cavity 22 (or balloon 52) and the instrument according to the present invention is removed, 79.

Modifications and substitutions made by one of ordinary skill in the art are within the scope of the present invention, which is not limited except by the claims which follow.

What is claimed is:

1. An ablation apparatus, comprising:

an elongated member having a first end configured to radiate microwave energy and a second end configured to receive microwave energy from a microwave source;

a sleeve having an inner and outer surface, and a length, and comprising a microwave absorbing material covering along its length and directly in contact with said first end configured to radiate microwave energy, and is configured to radiate heat energy in response to said radiated microwave energy; and a liquid delivery member disposed to provide a flow of liquid only over and around said sleeve outer surface proximal to and heated by contact with said sleeve which includes said microwave absorbing material, and said flow of liquid receiving said heat energy radiated by said sleeve, to be configured to ablate surrounding tissue by the heated flow of liquid, wherein said sleeve is disposed to separate said elongated member from said flow of liquid, and said sleeve inner surface faces said elongated member first end and said sleeve outer surface faces away from said elongated member first end.

2. The apparatus of claim 1, further including a drain member disposed to evacuate said liquid from said flow of liquid.

3. The apparatus of claim 1, further including a covering tube retaining said elongated member and said liquid delivery member.

4. The apparatus of claim 3, wherein said covering tube has an open end from which said elongated member emerges, further including an open end seal to restrict liquid flow into said covering tube open end.

5. The apparatus of claim 1, wherein said liquid comprises one or more of distillate water, dextrose in water, and saline or liquid with microwave absorbing particles.

6. The apparatus of claim 1, wherein said microwave absorbing material permits a portion of said microwave energy to pass through into said liquid, and said liquid absorbs said portion of said microwave energy.

7. The apparatus of claim 1, wherein said microwave absorbing material comprises a microwave transparent material and microwave absorbing particles in said microwave transparent material.

8. The apparatus of claim 7, wherein the microwave transparent material comprises at least one of ceramic, silicone, fluorosilicone, fluorocarbon, thermoplastic rubber, ethylene propylene diene monomer, and urethane.

9. The apparatus of claim 7, wherein said microwave absorbing particles comprise at least one of nickel (Ni), copper (Cu), Aluminum (Al), Ag/Cu; Ag/Al; Ag/Ni; Ag/Glass, nickel-plated graphite, silver-plated aluminum, silver-plated copper, silver-plated nickel, silver-plated glass and pure silver.

10. The apparatus of claim 1, wherein the microwave absorbing material comprises one of a silicone elastomer having a Ni/Cr filler, and a silicone elastomer with nickel particles dispersed in it.

11. The apparatus of claim 1, further including a temperature sensor disposed to monitor the temperature of said liquid and connected to stop or slow the supply of microwave energy to the antenna when said liquid reaches a selected temperature.

12. An ablation apparatus, comprising:

an elongated member having a first end configured to radiate microwave energy and a second end configured to receive microwave energy from a microwave source;

a sleeve having an inner and outer surface, and a length, and comprising a microwave absorbing material covering along its length and directly in contact with said first end configured to radiate microwave energy, and is configured to radiate heat energy in response to said radiated microwave energy; and a liquid delivery member disposed to provide a flow of liquid only over and around said sleeve outer surface proximal to and heated by contact with said sleeve which includes said microwave absorbing material, and said flow of liquid receiving said heat energy radiated by said sleeve, to be configured to ablate surrounding tissue by the heated flow of liquid, wherein said sleeve is disposed to separate said first end configured to radiate microwave energy from said flow of liquid, and said sleeve inner surface faces said first end configured to radiate microwave energy and said sleeve outer surface faces away from said elongated member first end.

13. The apparatus of claim 1, further comprises a balloon covering said elongated member first end and disposed to contain said flow of liquid introduced by said liquid delivery member.

14. The apparatus of claim 13, wherein said balloon comprises a rubber-like material.

15. The apparatus of claim 13, further including a outside tubing retaining said elongated member and said liquid delivery member and having an open end, wherein said balloon includes an open end disposed to surround said outside tubing open end.

* * * * *